United States Patent
Zelickson et al.

(10) Patent No.: US 6,645,184 B1
(45) Date of Patent: Nov. 11, 2003

(54) TAPE STRIPPING SYSTEM AND METHOD

(76) Inventors: Brian D. Zelickson, 2764 Drew Ave., Minneapolis, MN (US) 55416; David A. Kist, 1077 22nd Ave. SE., Minneapolis, MN (US) 55414

( * ) Notice: Subject to any disclaimer, the term of this patent is extended or adjusted under 35 U.S.C. 154(b) by 215 days.

(21) Appl. No.: 09/635,285

(22) Filed: Aug. 9, 2000

Related U.S. Application Data

(60) Provisional application No. 60/147,916, filed on Aug. 9, 1999.

(51) Int. Cl.[7] .............................................. A61M 35/00
(52) U.S. Cl. ...................................... 604/290; 606/131
(58) Field of Search ................................ 604/289, 290; 606/131

(56) References Cited

U.S. PATENT DOCUMENTS

| | | | | |
|---|---|---|---|---|
| 4,040,414 A | | 8/1977 | Suroff ........................ 128/24 |
| 4,447,482 A | | 5/1984 | Heinzelman et al. ...... 428/42.3 |
| 4,572,187 A | | 2/1986 | Schetrumpf ................ 128/355 |
| 4,752,472 A | | 6/1988 | Kligman .................... 424/81 |
| 5,037,432 A | | 8/1991 | Molinari .................... 606/131 |
| 5,383,900 A | * | 1/1995 | Krantz ....................... 606/215 |
| 5,685,833 A | | 11/1997 | Turngren .................... 602/58 |
| 5,720,963 A | | 2/1998 | Smith ........................ 424/401 |
| 5,935,596 A | * | 8/1999 | Crotty et al. ............... 424/401 |
| 5,964,749 A | | 10/1999 | Eckhouse et al. ............ 606/9 |
| 5,971,999 A | | 10/1999 | Naldoni ...................... 606/131 |
| 6,039,745 A | | 3/2000 | DiFiore et al. ............. 606/131 |
| 6,080,165 A | | 6/2000 | DeJacma .................... 606/131 |
| 6,106,818 A | * | 8/2000 | Dulog et al. ................ 424/401 |
| 6,113,559 A | | 9/2000 | Klopotek .................... 601/3 |
| 6,136,008 A | * | 10/2000 | Becker et al. .............. 600/392 |
| 6,139,553 A | | 10/2000 | Dotan ......................... 606/131 |
| 6,221,382 B1 | * | 4/2001 | Ishida et al. ................ 424/443 |
| 6,228,487 B1 | * | 5/2001 | Howard et al. ............. 424/401 |
| 6,391,034 B1 | * | 5/2002 | Adamson et al. ........... 606/131 |

FOREIGN PATENT DOCUMENTS

| | | |
|---|---|---|
| DE | 29803828 | 3/1998 |
| FR | 2063743 | 7/1971 |
| FR | 2 773 461 | * 1/1998 |
| WO | WO 00/15300 | 3/2000 |

* cited by examiner

*Primary Examiner*—Weilun Lo
*Assistant Examiner*—Michael G. Bogart
(74) *Attorney, Agent, or Firm*—Fredrikson & Byron, PA

(57) ABSTRACT

A system and method for utilizing tape-like material by applying it to human skin and then stripping the tape from the skin to remove excess or unwanted material. The system further includes application of other elements to facilitate skin recovery and rejuvenation processes.

12 Claims, 3 Drawing Sheets

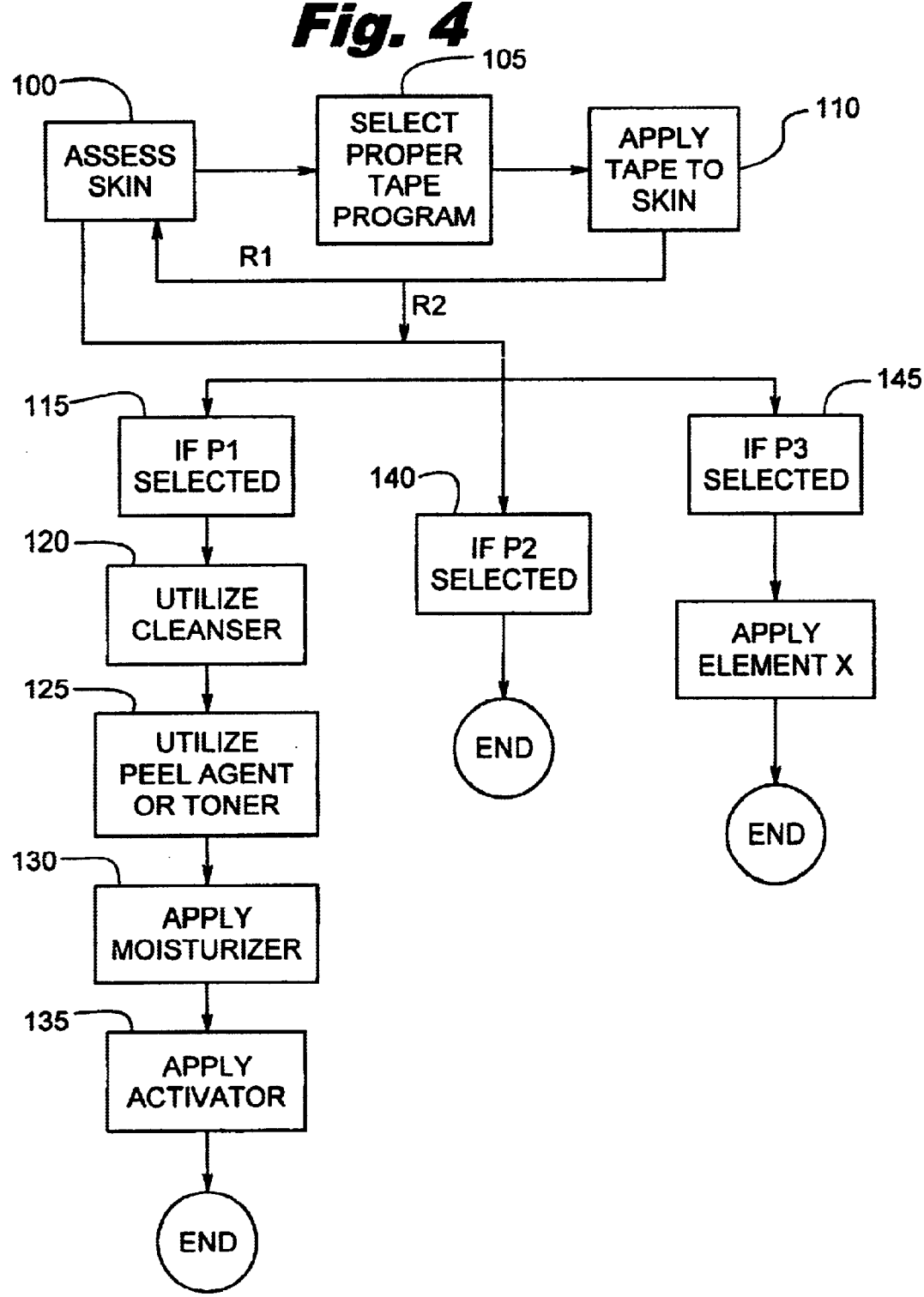

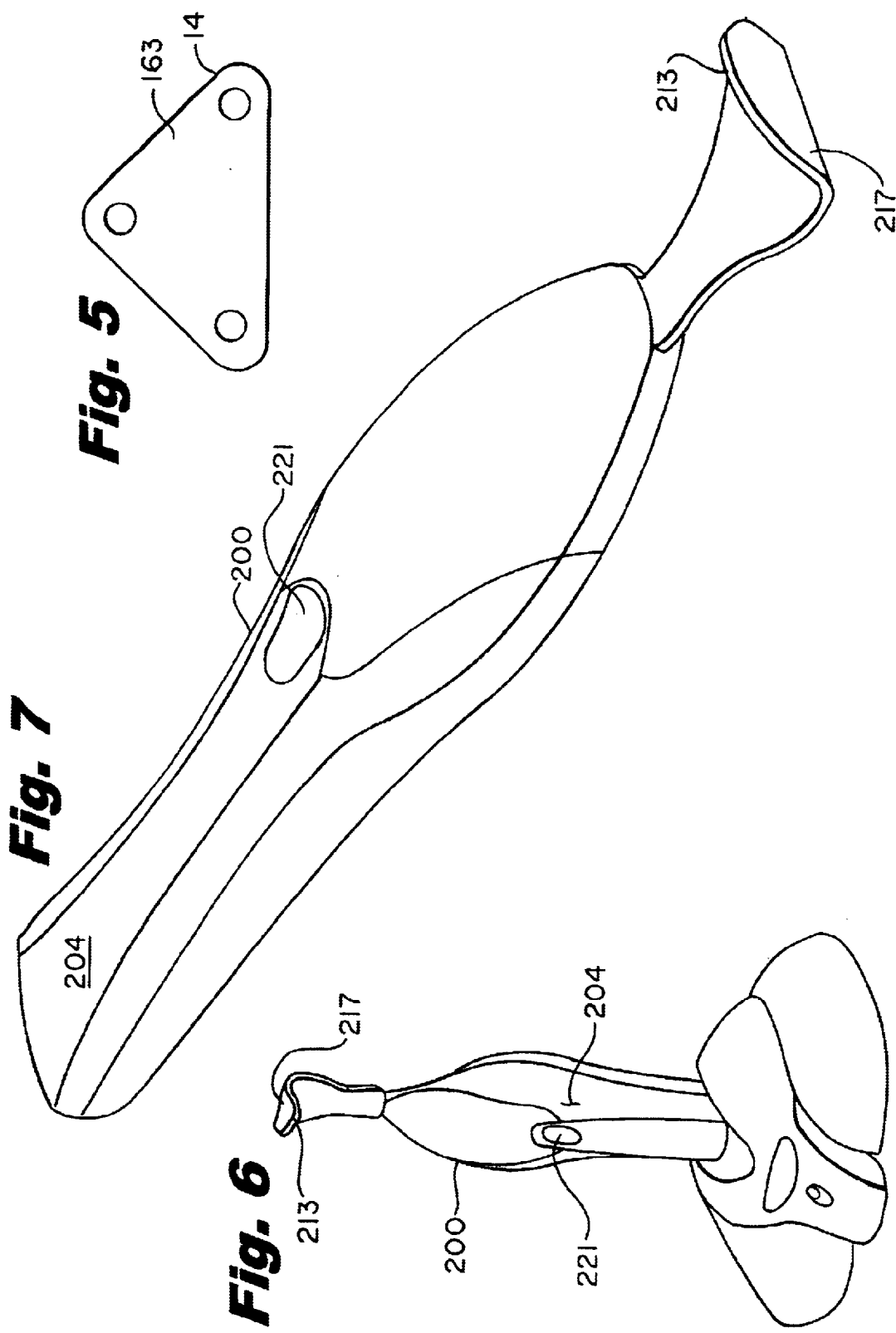

TAPE STRIPPING SYSTEM AND METHOD

CROSS-REFERENCED APPLICATION

This Application claims priority to U.S. Provisional Application No. 60/147,916 filed Aug. 9, 1999.

FIELD OF THE INVENTION

The invention relates to apparatus and methods for cleaning and rejuvenating skin.

BACKGROUND OF THE INVENTION

Various environmental and natural occurrences result in blemishes and wrinkles to human skin. For example, sun exposure, chronic irritation due to many different causes, and neglect may all cause skin problems. Recent advances in laser and chemical treatments have been successful in improving the appearance of the treated skin but these methods are rather labor intensive and can be traumatic.

One approach by medical practitioners includes the use of micro-dermabrasion techniques to treat skin blemishes. Although quite effective in certain applications, this technique can be risky and requires specially licensed operators.

Another approach by medical and cosmetic practitioners includes the use of adhesive-type tape applied to the patient's skin so that when the tape is removed the tape also removes an upper portion of the skin. This form of procedure is referred to as barrier disruption. Some analyses have suggested that barrier disruption by cellophane tape stripping triggers a cascade of biochemical activity which serves to "turn over" structural proteins that constitute human skin. For example, such tape stripping may stimulate the production of keratins 6,16,17 and reduce the mount of keratins 5 and 14, while also prematurely expressing involucrin. Yet another analysis suggests that tape stripping increases the rate of transepidermal water loss by 100 times the normal rate. In yet another analysis, tape stripping is suggested as having a regulatory effect upon fatty acid transport proteins and fatty acyl CoA synthase.

This data suggests that biochemical activity occurs following tape stripping which may be related to long term skin restructuring. An immediate consequence is the removal of redundant scale, plaques, and comedones which results in a rejuvenated appearance.

SUMMARY OF THE INVENTION

A tape roller is provided for a user to self-administer the tape to portions of the user's skin. This facilitates the, removal of elements of the skin and facilitates self-administration of other skin agents or to simply improve the health or appearance of the user's skin. A system and method of integrated skin care is provided which relies on the effective and easy removal of upper skin detritus.

BRIEF DESCRIPTION OF THE DRAWINGS

FIG. 4 is diagram depicting a preferred system and methodology for administration of skin care using the tape removal concept of this invention.

FIG. 5 is a bottom plan view of a tape dispenser.

FIG. 6 is a perspective view of an embodiment of the invention, with a charging unit.

FIG. 7 is a perspective view of an embodiment of the invention.

DETAILED DESCRIPTION

Figure 1:
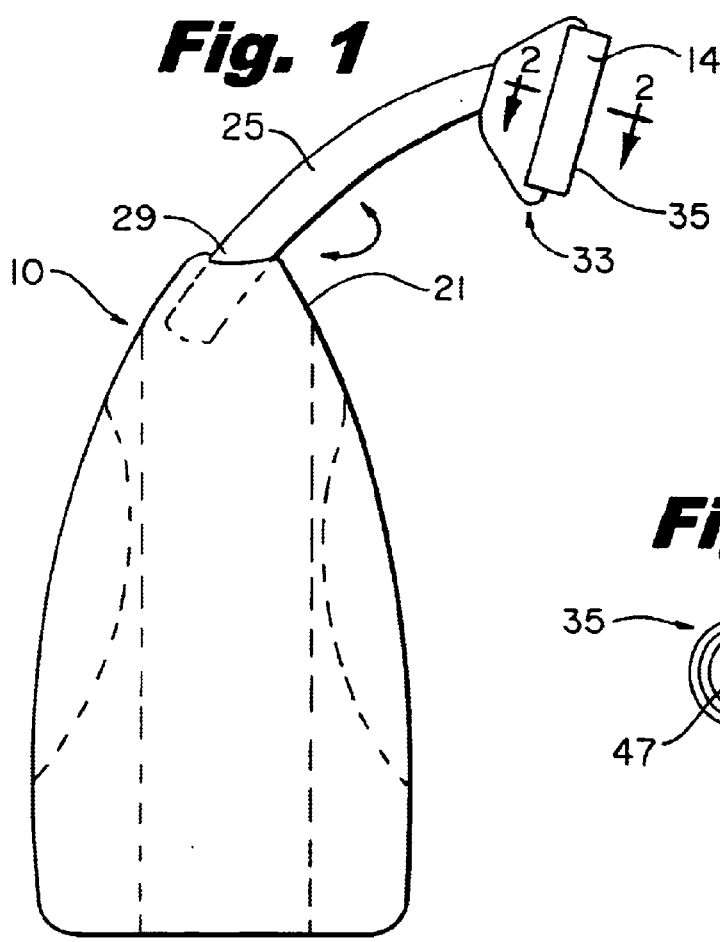
FIG. 1 is a perspective view of a handheld apparatus for self-administration of tape to skin.

FIG. 1 is a perspective view of a handheld apparatus 10 for self-administration of a tape-like product 14 to skin. Apparatus 10, also referred to as system 10, includes, in one embodiment, a handheld ergonomically structured device 21. Handheld device 21 comprises a body portion having a variety of optional shapes and configurations, as depicted by representative dashed lines, although not limited to said precise configurations. Most importantly, the body portion shape must conform to a comfortable gripping configuration of a user's hand when using the device for self-administration at or about the facial area, as well as other body portions. For this reason, it is recognized that extension 25 may be formed as a unitary part with the body portion, or it may be separately attached and/or inserted at various locations on body portion, such as at neck 29, or other locations. Suitable attaching and locking means are contemplated in the event that extension 25 forms a piece separate than the body portion. Regardless, a tape dispensing holder is positioned at a distal end 33 of extension 25. This feature comprises any of various retaining means suitable for holding and dispensing a rolled tape unit 35. It is appreciated that extension 25 may be made of a material that has a memory suitable for reconfiguring by each user, possibly through use of advanced technology material such as that similar to a nitinol-type of material or one with suitable reshaping characteristics, or it may be simply be manufactured to have a curvilinear or other shape suitable for a single design optimized for all users.

Figure 2:
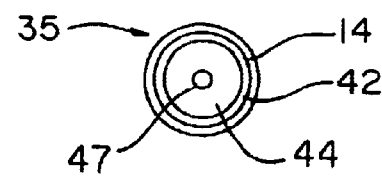
FIG. 2 is a section view of a tape roll taken along lines 2—2 of FIG. 1.

As shown in FIGS. 1 and 2, rolled tape unit 35 comprises a cylindrical-style roll of material forming at least one outer layer of tacky material, referred to herein as tape. The outer tacky material of rolled tape unit 35 is designed for dispensing along the surface of the user's skin, preferably facial skin, in order to remove detritus and other undesired material from the surface of the skin. Indeed, according to the various programs of usage and degree of tackiness of the tape, it is possible to remove both scales and external environmental pollutants as well as portions of the skin itself. In one embodiment it is also conceivable to have multiple layers of tape, for example, as shown in FIG. 2 at layer 42. In this embodiment it is possible to utilize the same rolled tape unit 35, but extend its life by removing a used outer layer of tacky tape material 14 and exposing an unused tacky layer of tape material 42 for subsequent use, or at the subsequent use time. Layer or volume 44 of rolled tape unit 35 may simply comprise additional layers of tape or it may provide a spacer having various material properties. For example, one type of spacer may include a resilient material to reduce the rigidity and increase the tactile affection of the user and the product being applied to the user's skin.

Either a dimple or full channel may comprise the most efficacious means of allowing the rolled tape unit to function along with the distal end dispensing portion of the handheld device. Such dimple or channel is represented by element 47 in FIG. 2.

Figure 3:
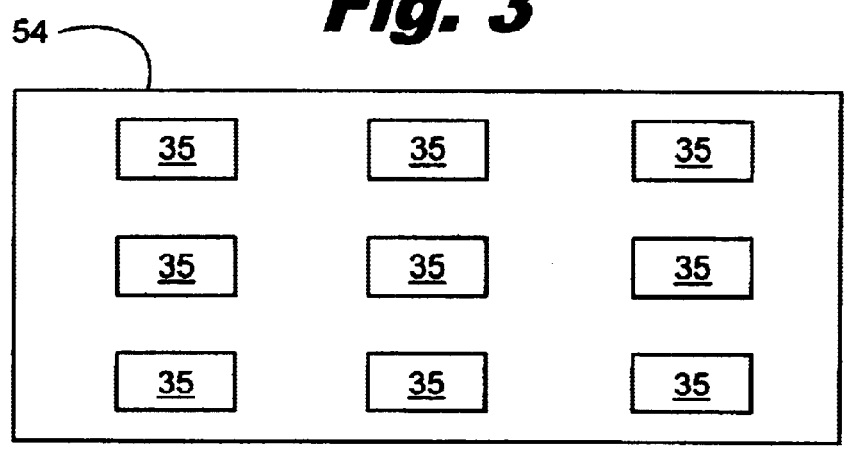
FIG. 3 is a plan view of an exemplary dispenser of tape rolls.

FIG. 3 discloses dispensing pack 54 designed for holding and dispensing one or more rolled tape units 35. In one embodiment, dispensing pack 54 may be structured with opening and closure layers similar to those packages known in the dispensing industry as blister packs. In this embodiment, the user simply presses on one side of dispensing pack 54 to release a single rolled tape unit 35 from the package. In that instance it is important that a cover layer (which is retaining the rolled tape unit within the package) to have a material or material coating suitable to prevent adherence to the rolled tape unit tacky layer. Alternatively, a non-tacky cover layer may be applied to each of the rolled tape units to facilitate storage, dispensing, and mounting on the handheld device prior to actual use against the skin. Then, in such an embodiment, the non-tacky layer is removed thus exposing the tacky tape material 14.

In the past, tape stripping technology has been limited to use by professionally trained medical and cosmetic practitioners. At least one objective of this invention is to facilitate use by the individual user independent of the inconvenience, high cost, and lack of privacy implications of requiring office visits and the like in order to receive the benefits of this technology. Rather, as shown in FIG. 4, it is now possible to utilize the dispensing and individualized tape roller system disclosed in FIGS. 1–3 to allow individual users the chance to receive this treatment through self-administration. However, it is quite important to recognize that a methodology is recommended, and that such methodology has various options. As in most medical device, therapeutic, or other systems which relate to individual user preferences and morphology, there are various algorithms which apply to each individual user. FIG. 4 demonstrates an example of the algorithmic approach to use of this technology.

Block 100 represents the proper first step or method which requires careful assessment of the user's skin history, skin type, current skin condition, and usage goals of the system. After such proper assessment is completed by the user, he or she then selects the proper tape program according to the assessment of block 100. For example, one type of program (referred to herein as "P1") comprises a comprehensive rejuvenation program as later discussed below. Alternatively, a second tape program (referred to herein as "P2") comprises use of a tape-like material 14 having certain medications, such as an antibacterial material or a cortisone material imbedded in the tape and configured for release upon application to the skin. Yet another tape program (referred to herein as "P3") which may be appropriate for the particular user includes application of one or more elements to the skin following the initial tape application and removal. Such elements are also discussed below.

Following assessment of the skin and selection of the proper tape program according to the goals of the user, then the user applies the tape-like material 14 to the skin at the appropriate areas using, in one embodiment, the handheld device and roller system shown in FIG. 1. It is recognized that alternate dispensing means may be provided consistent with facilitating self-administration and ease of access to the various sites of interest on highly variable body morphologies. In a general sense however, this invention is designed to a great extent to facilitate the tape application to and removal from portions of a human facial skin area. Accordingly, a preferred ergonomic design may be found under the various options as shown in FIG. 1 to facilitate gripping in a comfortable manner, particularly at an early or late part of a user's day when the hand may be less comfortable or more stiff for various reasons.

Following application of the tape to the skin, a skin assessment is again recommended under the pathway R1 shown in FIG. 4. It is understood, however, that the skin assessment at this point in the procedure may be bypassed, particularly by experienced users. In this instance, pathway R2 directs the user to one of several program options P1, P2, or P3.

If the user selects tape program PI, then this program may include use of a cleanser 120, followed by a peel agent or toner 125, followed by an optional moisturizer 130, and then application of an activator 135. Examples of activators may include active lotions or materials such as those including vitamins or other rejuvenating elements. Alternatively, if the user selects tape program P2, then that user has chosen to utilize either a standard tape-like material 14 or a tape-like material 14 having additional medications imbedded or otherwise positioned on the tape. This latter configuration facilitates application of such medication while also removing the detritus or other tissue as discussed above during the same application of the tape. Regardless of which of the sub-options of step 140 of program 2 is selected, there is no need to proceed to any other substeps following application of the tape and removal of the tape from the skin.

However, if the user selects proper tape program P3 as shown at block 145, then the user may wish to followup the tape application and removal step with application of one of various types of elements, herein referred to as element X. For example, a topical anesthetic, a medication, a toning agent, a moisturer, an activator, or even simply a cleanser, or even a splash of water may be appropriate for use as element X. It is also recognized that element X may also include a second application and/or subsequent applications of the tape to the skin within the context of this disclosure.

It is recognized therefore that system 10 is useful for dispensing tape means having various adhesive or tacky features on the tape. This tape is designed to remove excess skin cells or other material from the surface of skin in order to rejuvenate and stimulate that skin. A disposable single use type application is possible within the scope of this invention, and is quite appropriate in view of the increased environmental challenges and air particulate encountered every day by users. This self-administration product is particularly useful for home users for smoothing, refreshing, and regenerating damaged skin at a much lower cost than lasers, chemical peels or micro-derm abrasion. Indeed, the advantages of the embodiments of this technology shown in this application are quite distinct even over specific tape stripping by professional medical or cosmetic providers in a medical or cosmetic office environment. Regardless, no system exists for teaching and guiding the self user in the efficacious uses of a tape stripping system. This invention overcomes the failings of any prior art in providing simple and effective means for rejuvenating human skin in a manner appropriate to each individual user.

Further embodiments of handheld apparatus 10 may be configured in non-circular tape dispensing figurations, such as tape dispenser 163 shown in FIG. 5, having a tape-like product 14. The devices of the invention disclosed herein may also function as a rolling tape application motion, or as circular, or reciprocating, provided that the required skin to tape interface is achieved.

FIGS. 6 and 7 illustrate an embodiment of the invention comprising handheld apparatus 200. Handheld apparatus 200 is designed to provide an ergonomic gripping handle 204, having internal charging and motion generating means, generally of conventional type similar to that found in mechanical or electrical toothbrush mechanisms, but with a capability of causing or imparting motion to an applicator tip or component 213. Applicator tip or component 213 may be configured so that it is removable and reconfigurable, as desired. In one embodiment, component 213 is designed to have a surface 217 configured to receive tape-like material, such as disclosed herein above in the tape stripping system, with the tape-like material suitable for abrading and applying Medications as disclosed herein. In operation, device 200 is held by the user while component 217, which has previously been configured with a tape-like material having the appropriate abrasion characteristics, and the user activates the motion of the component 213 using various activation means such as, for example, activating mechanism 221. Following activation, component 213 is set in motion in either a reciprocating, circular or other fashion so as to effect the appropriate abrasion using the tape-like material on the user's skin. In an alternate use, the user may remove an abrading tape-like material and instead apply a buffing or polishing type strip on face 217 to effect further penetration or other desired effects upon the skin being treated. As shown in FIG. 6, one embodiment of this device includes a charging stand which may be suitable for providing electric generating means to a rechargeable battery within the gripping portion of the device. Yet another embodiment includes, for example, a device 200 which does not have the internal mechanisms described herein above in relation to this handheld device but rather has a remote connection, such a wired connection, with a remotely configured motor or motion generating means which may be selectively applied by cord or wireless to the handheld device, thereby imparting the motion of applicator face 217 independent of the possible cumbersome size of an internally located motion generating mechanism.

It has also been appreciated by the inventors that the system, device components, and methods described above are useful for hair removal, drug delivery, and serum extraction for diagnostic and related purposes. Accordingly, the disclosure of the invention contemplates claims to these aspects of the invention as well.

What is claimed is:

1. A method of rejuvenating skin comprising the steps of:
   assessing the skin to be rejuvenated;
   selecting a proper tape program for application and removal of tape to a surface of an applicator tip of an ergonomically shaped handheld apparatus;
   applying an appropriate tape to the surface of the applicator tip;
   setting in motion the applicator tip throughout the time that the applied tape is in contact with the treated area of the skin; and
   implementing the selected tape program so that the motion of the applicator tip and the tape on the applicator tip impacts a rejuvenating effect on the skin being treated.

2. The method of claim 1 in which the selected tape program determines the motion of the device and the tape in contact with a user's skin.

3. A skin rejuvenating, system for a user's skin, comprising:
   an ergonomically shaped handheld device having motion generating means for imparting desired motion to a partially inserted component at a distal tip thereof, and a distal tip surface having wall portions defining, a connection aperture for connecting a rejuvenating surface component portion into said distal tip area aperture, and a handheld hand actuatable motion generating and control means; and
   a distal component having a first portion designed for insertion into a motion generating subsystem of the handheld device, and a second portion having a shaped configuration to conform to a user's skin surface, with said conformed surface comprising means for placing a skin treatment surface element material on said surface to apply energy to the user's skin suitable to regenerate portions of the skin.

4. A method of using a comprehensive rejuvenation program for rejuvenating skin comprising the steps of:
   assessing the skin to be rejuvenated and the intended rejuvenation goal;
   selecting a proper therapeutic algorithm from a selection of algorithms which is appropriate for a particular user;
   selecting a disposable surface element for application of a skin treatment product, said element having at least one surface designed for applying a penetrating and rejuvenating effect on a skin area being treated;
   configuring the skin treatment product element on an ergonomically shaped re-usable handheld device portion suitable for receiving motion generating energy; and
   applying motion generating energy to said handheld device portion while the skin treatment product element is in contact with the skin to be rejuvenated so that the element is in moving contact with the skin and generates rejuvenation by restructuring and regeneration of skin.

5. The method of claim 4 in which the motion generating energy imparts a reciprocating motion to the element in contact with the skin.

6. The method of claim 4 in which the motion generating energy imparts a circular motion to the element in contact with the skin.

7. The method of claim 4 in which the motion generating energy imparts a buffing motion to the element in contact with the skin.

8. The method of claim 4 in which the motion generating energy imparts a polishing motion to the element in contact with the skin.

9. The method of claim 4 in which the motion generating energy imparts a regenerating motion to the element in contact with the skin so that the element actually regenerates damaged skin rather than creating an appearance of rejuvenated skin.

10. The method of claim 4 in which the skin treatment product surface element is selected from a cleanser, a peel agent, a toner, a moisturizer, an activator, an abrasive, a buffing material, a polishing material, and a medicament.

11. A combination therapy method for rejuvenating skin comprising the steps of:
   assessing the skin to be rejuvenated and the intended rejuvenation goal;
   selecting a proper therapeutic algorithm from a selection of algorithms which is appropriate for a particular user;
   selecting a disposable surface element for application of a skin treatment product, said element having at least one surface designed for applying a penetrating and rejuvenating effect on a skin area being treated;
   configuring the skin treatment product element on an ergonomically shaped re-usable handheld device portion suitable for receiving motion generating energy;
   applying motion generating energy to said handheld device portion while the skin treatment product element is in contact with the skin to be rejuvenated so that the element is in moving contact with the skin and generates rejuvenation by restructuring and regeneration of skin; and re-assessing the skin to be rejuvenated to identify further treatment required.

12. The method of claim 11 in which the combined therapy comprises selection and use of a plurality of skin treatment product elements including an abrasive to remove a surface portion of the skin, an application of appropriate energy to regenerate a portion of the skin, and a third element to either medicate or moisturize a portion of the skin.

* * * * *